United States Patent [19]

Yang et al.

[11] Patent Number: 4,705,848
[45] Date of Patent: Nov. 10, 1987

[54] ISOLATION OF BIOACTIVE, MONOMERIC GROWTH HORMONE

[75] Inventors: Ren-Der Yang; Edwin J. Hamilton, Jr., both of Terre Haute; Larry D. Taber, Indianapolis, all of Ind.

[73] Assignee: International Minerals & Chemical Corp., Terre Haute, Ind.

[21] Appl. No.: 869,702

[22] Filed: Jun. 2, 1986

[51] Int. Cl.$^4$ .............................................. A61K 37/36
[52] U.S. Cl. .................................... 530/399; 530/397; 530/808; 530/825
[58] Field of Search ................. 530/399, 397, 808, 825

[56] References Cited

U.S. PATENT DOCUMENTS

| 4,511,502 | 4/1985 | Builder et al. | 260/112 R |
| 4,511,503 | 4/1985 | Olson et al. | 530/399 X |
| 4,512,922 | 4/1985 | Jones et al. | 530/399 X |
| 4,518,526 | 5/1985 | Olson | 530/399 X |

FOREIGN PATENT DOCUMENTS

| 0116778 | 6/1984 | European Pat. Off. . |
| 0114507 | 8/1984 | European Pat. Off. . |
| 0122080 | 10/1984 | European Pat. Off. . |
| 0121775 | 10/1984 | European Pat. Off. . |
| 0123928 | 11/1984 | European Pat. Off. . |
| WO83/04418 | 12/1983 | PCT Int'l Appl. . |
| WO84/03711 | 9/1984 | PCT Int'l Appl. . |
| 2129810 | 5/1984 | United Kingdom . |

*Primary Examiner*—Howard E. Schain
*Attorney, Agent, or Firm*—Wendell R. Guffey; Peter R. Shearer; Thomas L. Farquer

[57] ABSTRACT

Monomeric, biologically active growth hormone is isolated from microbially-produced insoluble inclusion bodies by solubilizing and denaturing the growth hormone by extraction of the inclusion bodies into a guanidine salt solution such as guanidine hydrochloride and subsequently renaturing at least a portion of the growth hormone in the solution by replacing the guanidine salt solution with a denaturant-free buffer solution and removing precipitated impurities and growth hormone aggregates. The renatured growth hromone is then purified by ion-exchange chromatography.

19 Claims, No Drawings

ISOLATION OF BIOACTIVE, MONOMERIC GROWTH HORMONE

BACKGROUND OF THE INVENTION

The advent of recombinant DNA technology has made possible the large scale production of proteins by the insertion of heterologous, protein-encoding genes into microorganisms such as bacteria and expression of the genes within the host microorganisms. In this manner, a large variety of proteins, including some which can only be obtained in minute quantities from natural sources, can be economically produced in unlimited quantities.

Unfortunately, proteins which are native to eukaryotic cells may not undergo post-translational processing in microbial hosts to yield biologically active forms of the desired proteins. Thus, for example, eukaryotic proteins containing multiple cysteine residues may not form the correct disulfide linkages necessary for biological activity when they are expressed in microbial hosts. Not only may the eukaryotic protein fold improperly within the intracellular environment of the host, but also the individual molecules may form biologically inactive aggregates or oligomers as the result of the formation of intermolecular disulfide bonds or other types of intermolecular bonding.

As the result of one or more of these phenomena—improper folding, incorrect disulfide bond formation and non-covalent or covalent oligomerization—many proteins that are produced by the expression of heterologous genes in microbial hosts are not recovered from the host cells in the form of soluble, biologically active protein. Rather, upon lysis of the cells, the heterologous proteins are found in the form of insoluble "inclusion bodies," also sometimes referred to as "refractile bodies." In order to produce useful proteins, a means must be provided whereby the inclusion body proteins can be converted into a monomeric, biologically active form in which they are soluble in biological fluids.

In addition to converting the inclusion body proteins into soluble, monomeric, biologically active forms, it is necessary at some point in the recovery process to purify the protein in order to remove bacterial impurities including endotoxins, other bacterial proteins and contaminating substances derived from the bacterial host and/or the fermentation medium. This is usually done by subjecting the protein to some of the various chromatographic purification procedures such as ion-exchange chromatography.

PCT Application No. GB 83/00152 discloses methods for recovering and activating the milk-clotting enzyme chymosin, beginning with inclusion bodies produced in *E. coli* which contain the enzyme in its zymogenic form. The methods involve dissolving the inclusion body protein in denaturants such as urea, guanidine hydrochloride or alkali solution, renaturing the protein by removing or diluting the denaturant and reducing the pH of the solutions to induce autocatalytic cleavage of the zymogen to the mature form of the protein.

Solubility and folding characteristics vary considerably between different proteins, since both are highly dependent on the primary structure, i.e., amino acid sequence, of the protein. It has been the experience of the prior art that animal growth hormones are particularly difficult proteins to recover in soluble, monomeric, biologically active form. Thus, for example, it is said in U.S. Pat. No. 4,512,922 that, for proteins such as growth hormones, dissolution of the inclusion body protein in a strong denaturant followed by dilution of the denaturant with aqueous buffer almost invariably results in reprecipitation of the protein. Even if reprecipitation does not occur, expected levels of activity are said not to be shown. As a solution to this problem, there is disclosed a method for purifying growth hormone in which the inclusion body proteins are solubilized in a strong denaturant; the strong denaturant is replaced by a weaker denaturant; and the weaker denaturant is subsequently removed to renature the protein.

We have found that a two-stage renaturation process, such as that disclosed in U.S. Pat. No. 4,512,922, entails a number of problems. The yields of soluble, biologically active growth hormone obtainable are not particularly good. Moreover, the method yields varying results depending on the species of growth hormone involved. For example, using 8 M guanidine hydrochloride as a strong denaturant and 3.5 M urea as the weaker denaturant, we have found that yields of soluble, biologically active porcine growth hormone were only on the order of about 1% or less. While bovine growth hormone yields were somewhat higher, on the order of about 5%, these were still only marginal from a commercial point of view. Moreover, problems arose in the purification of the proteins recovered by this process. When the proteins recovered in this manner were loaded onto an ion-exchange column for purification, large quantities of soluble protein aggregates bound to the column, causing it to become fouled and obstructed within a relatively short period of time. This was true even when the column purification was carried out under reducing conditions in an attempt to eliminate aggregates. The use of the two-stage renaturation process is also problematical from a commercial production standpoint inasmuch as it entails numerous processing steps and expensive reagents.

We have also attempted to recover growth hormones from inclusion bodies by solubilizing the inclusion body proteins in 8 M urea and subsequently renaturing the protein in a single step by dialysing the solution against denaturant-free buffer to remove the urea. Yields of recovered monomeric growth hormone were very poor, that is, on the order of 1% or less.

It is an object of this invention to provide an efficient method for recovering microbially produced growth hormone in a soluble, monomeric, biologically active form.

It is a further object of the invention to provide a method for recovering and purifying microbially produced growth hormone using a chromatographic purification column whereby the purification column does not become plugged and obstructed within a short period of time.

Other objects and advantages of the invention will be readily apparent from the description of the invention which follows.

SUMMARY OF THE INVENTION

This invention provides an efficient, economical method for isolating and purifying soluble, bioactive, monomeric growth hormone from inclusion bodies. The method of the invention avoids many of the problems associated with the two-stage renaturation or urea-based methods of the prior art. In particular, the process of the invention substantially reduces the presence of soluble GH aggregates and thus alleviates the problem of column fouling during ion exchange chromatography. Furthermore, the process of the invention reduces the number and cost of reagents used in the recovery process.

Contrary to the teachings of the prior art, we have found that under appropriate conditions, growth hormone inclusion bodies can be solubilized in a guanidine salt solution and thereafter renatured by a single-step removal of guanidine. When guanidine is removed in a rapid single-step renaturation, essentially all protein aggregates precipitate from the solution, allowing them to be separated from soluble, monomeric growth hormone prior to chromatographic purification. Consequently, fouling and obstruction of the column is minimized and the useful life of the column is extended.

In the practice of the invention, the inclusion body is solubilized and the protein denatured by extracting it into an aqueous solution of a guanidine salt preferably guanidine hydrochloride. The guanidine salt solution is then replaced by denaturant-free buffer solution, for example, by dialysis, causing at least a portion of the denatured growth hormone to refold to its monomeric, native configuration. Concomitantly, some proteinaceous contaminants as well as almost all growth hormone aggregates which may be present in the solution are precipitated. The precipitated contaminants and aggregates are easily separated and the remaining solution of monomeric growth hormone, in its biologically active form, is then further purified by ion exchange chromatography. The replacement of guanidine salt with denaturant-free buffer solution is carried out without the use of an intermediate denaturant. In a commercial scale production process, elimination of the intermediate denaturant represents a substantial savings in material costs.

DETAILED DESCRIPTION OF THE INVENTION

The process of the invention can be employed in the isolation of monomeric, biologically active forms of any animal growth hormones which are found as insoluble inclusion bodies in microorganisms, such as bacteria, particularly bovine growth hormone (bGH) or porcine growth hormone (pGH), including biologically active fragments thereof and analogs which have differences in amino acid sequence but still display growth hormone activity.

Methods for preparing expression vectors capable of expressing growth hormone in bacterial hosts are known in the art (see, e.g., Seeburg et al., *DNA*, 2:37–45 [1983] and Goeddel et al., *Nature*, 281:544–548 [1979]). In one embodiment of the process of the invention, we used pGH-containing inclusion bodies which were produced by an *E. coli* host strain HB101 transformed with a first plasmid, pL-mu-Δ7 SGH, coding for Δ7 pGH (porcine growth hormone less its seven N-terminal amino acids plus methionine and serine) under the control of a phage lambda promoter and a second plasmid, pCI857, which codes for the temperature-sensitive lambda phage repressor protein. In another embodiment, we employed bGH-containing inclusion bodies which were produced by an *E. coli* host strain HB101 transformed with a plasmid, pL- mu-Δ9 bGH, coding for Δ9 bGH (bovine growth hormone less its nine N-terminal amino acids plus methionine and serine) and with plasmid pCI857. It will be readily apparent, however, that the process of this invention is equally applicable to the purification of recombinant growth hormone produced by any host/vector combination, provided only that the growth hormone is produced in the host in the form of an insoluble inclusion body.

Prior to using the recovery and purification procedure of the invention, the transformant cells are generally lysed, either mechanically or enzymatically, to allow recovery of the inclusion bodies which are sequestered within the cells. The inclusion bodies can be separated from the bulk of the remainder of the cellular material by centrifugation and washing in a buffer. Preferably, the cell paste which is obtained by separating the cells from the fermentation medium is dispersed in an aqueous buffer solution containing ethylenediaminetetraacetic acid (EDTA) (20 millimolar) and monosodium phosphate (100 millimolar) adjusted with sodium hydroxide to pH 7.8. The cells are disrupted to release the growth hormone inclusion bodies by passage one or more times through a poppet-type homogenizer such as a Manton-Gaulin homogenizer. Growth hormone pellets are separated from the solution substrate and from some of the cell debris matter by centrifugation. The resulting pellets are washed one or more times by resuspension in an EDTA-monosodium phosphate buffer solution (10 millimolar EDTA, 0.2 molar $NaH_2PO_4$, adjusted to pH 7.5) and are separated from the wash solution by centrifugation. The resulting washed pellets are stored at about 4° C. if they are to be used within a few days or they are frozen if they are to be used at a later date.

The recovery procedures taught by the prior art generally employ wash steps that use detergents such as Triton X-100, reducing agents such as 2-mercaptoethanol and enzymes such as lysozyme in order to maximize the removal of cell debris and contaminating protein at the wash stage. We have found, however, that the use of such agents is unnecessary in the wash step. Moreover, their exclusion from the wash step is advantageous inasmuch as they cause some of the desired protein to be lost in the wash. Even though elimination of these agents from the wash allows some additional contaminants to be carried through to the solubilization step, we have found that some of these contaminants are precipitated later in the process without the use of any additional reagents.

The inclusion bodies containing the growth hormone are solubilized and the protein is denatured by extraction into an aqueous solution of a guanidine salt, preferably guanidine hydrochloride. Guanidine hydrochloride, which is a strong chaotrope, is capable of completely, but reversibly, denaturing proteins at concentrations of 6–8M. Advantageously, the guanidine hydrochloride solution is purified prior to use in the process of the invention in order to remove high molecular weight impurities which may be present. The impurities may be removed by ultrafiltration or by any other suitable purification means known in the art. Preferably, the solution also contains ethanolamine at a concentration of from about 20 mM to 100 mM. The inclusion bodies preferably are dissolved in the guanidine hydrochloride solution in an amount sufficient to give a concentration of growth hormone of from about 1 to about 2.5 grams per liter of solution. The solution is then allowed to stand for a sufficient amount of time to allow the completion of molecular unfolding. We have found that a period of from about 6 to about 36 hours is satisfactory.

After the growth hormone has been solubilized and denatured, at least a portion of the growth hormone in the solution is renatured by replacing the guanidine hydrochloride with denaturant-free buffer solution. Whereas the prior art teaches the slow removal of denaturant in order to maximize the amount of protein which remains in solution, we have found that a fairly rapid removal of guanidine salt is actually preferred because it reduces the presence of soluble protein aggregates in the renatured protein solution which tend to foul the chromatography column and which are not biologically active. Consequently, we prefer to remove the guanidine salt over a period of less than about 10 hrs. The ability to remove substantially all of the aggregated growth hormone as precipitate prior to ion-exchange chromatography is a major advantage of our method.

Replacement of the guanidine hydrochloride can be effected by any of the known methods for removing small molecules from protein solutions. Preferred methods for removing the guanidine hydrochloride include diafiltration and dialysis. We employ a hollow fiber ultrafiltration unit such as a Romicon HF4S, which is commercially available from Romicon, Inc. This unit employs a hollow fiber ultrafiltration membrane which allows the passage of molecules having molecular weights below about 10,000. The circulation of growth hormone solution past the ultrafiltration membrane results in the passage of guanidine hydrochloride solution through the membrane while the growth hormone is retained. The volume of solution is maintained by feeding a diluent solution containing ethanolamine at a concentration of about 60 millimolar adjusted to a pH of 9.0 to 9.8. The amount of diluent feed is about 5 to about 7 volumes per volume of growth hormone solution and the rate of feed is about 0.5 to about 4 volumes per hour. Accordingly, the flow rate of liquid amounts to about 120 liters per hour over 100 sq. ft. of membrane surface in the hollow fiber ultrafiltration unit.

Alternatively, the guanidine-containing solution can be diluted until the concentration of guanidine salt is so low that the growth hormone undergoes renaturation. This occurs at guanidine concentrations below about 1M.

As the guanidine hydrochloride is removed from the solution, some proteinaceous contaminants and growth hormone aggregates which are present precipitate from the solution. The precipitates can be removed from the solution by known methods such as centrifugation or filtration. If desired, the growth hormone solution may be concentrated somewhat by ultrafiltration prior to the centrifugation step.

The solution containing the soluble, monomeric growth hormone is purified by ion exchange chromatography. The ion exchange chromatography employs conventional equipment, such as a Pharmacia ion exchange column, which employs a DE-52 Cellulose ion exchange resin. The solution is loaded onto the column and the purified, bioactive growth hormone is collected in the run-through fraction which does not bind to the column.

Following ion exchange chromatography, the recovered growth hormone can be subjected to any conventional processing steps such as concentration by ultrafiltration, additional purification steps and, if desired, lyophilization to produce the growth hormone in a stable powdered form.

The following examples are intended to further illustrate the practice of the invention. Unless otherwise indicated, all percents are by weight and all temperatures are in degrees C.

EXAMPLE I

The transformant cells containing inclusion bodies of porcine growth hormone (pGH) that were used in this example were produced as follows:

Samples of $E.\ coli$ HB101 ($P_L$-mu-$\Delta 7$ SGH and pcI857) cells, ATCC 53031, to which 10% (v/v) glycerol had been added, were stored under liquid nitrogen or at -85° C. until needed.

A. Inoculation

The inoculum for a 9-liter fermentor charge was obtained by adding the cells to 200 ml of either ESM-1 or ESM-2 medium contained in a 500 ml flask. The pH of the medium was adjusted to a value of 7.0. The flask was closed with two milk filters so that some aeration of the medium could take place while the flask was shaken at 300 rpm for 16–20 hours at 30° C. in a New Brunswick Rotary Shaker.

| Ingredient | ESM-1 | ESM-2 |
|---|---|---|
| NZ Amine A | 16 g/L | 23 g/L |
| Glycerol | 30 | 30 |
| $KH_2PO_4$ | 5 | |
| $(NH_4)_2HPO_4$ | 2.5 | |
| $MgSO_4.7H_2O$ | 7 | 7 |
| $K_2HPO_4$ | | 6 |
| $(NH_4)_2SO_4$ | | 5 |
| $NaH_2PO_4$ | | 3 |
| Na Citrate | | 1 |
| Trace Element Solution* | 20 ml | 20 ml |

*Trace element solution G/L: EDTA 5, $FeCl_3.6H_2O$ 0.5, ZnO 0.05, $CuCl_2.2H_2O$ 0.01, $Co(NO_3)_2.6H_2O$ 0.01, $(NH_4)_2MoO_4$ 0.01.

B. Fermentor

The fermentor was a New Brunswick Microgen with a total volume of 16 liters. Nine liters of liquid medium was initially charged to the fermentor plus 180 ml of inoculum.

C. Fermentation Medium

The composition of the initial 9-liters of medium is shown below:

| Product | Concentration Grams per 9 Liters |
|---|---|
| NZ Amine A-Sheffield | 250 |
| Glycerol | 500 |
| $(NH_4)_2SO_4$ | 50 |
| $K_2HPO_4$ | 60 |
| $NaH_2PO_4$ | 30 |
| Na Citrate | 10 |
| $MgSO_4.7H_2O$ | 70 |
| Hodag K-67 antifoam | 4 ml |
| $FeCl_3.6H_2O$ | 0.1 g |
| ZnO | 0.01 g |
| $CuCl_2.2H_2O$ | 0.002 |
| $Co(NO_3)_2.6H_2O$ | 0.002 |
| $(NH_4)_2Mo\ O_4$ | 0.002 |
| EDTA (disodium salt) | 1.0 |

The medium was sterilized for 20 minutes at 121° C. and the pH was adjusted to 6.8 with NaOH.

To the medium 250 mg, each of ampicillin and kanamycin were added. The solution of antibiotics was sterilized by filtration.

D. Nutrient Feedings

At the time of induction, (i.e., when the temperature was raised to 42° C.), nutrients were added to the fermentation medium 250 g NZ Amine A (enzymatic casein hydrolyzate) and 200 g glycerol in approximately one liter water, were added. An additional feeding of 100 g NZ Amine A and 100 g of glycerol was given 5 hours post-induction.

E. Fermentor Operation

The operating conditions that gave us our best results are set forth in this section.

1. Growth Period 16–24 Hours a. Temperature of medium = 28°–30° C.
b. Agitator speed: 1000 RPM.
c. Energy input by the agitator 1.0–2.0 horsepower per 100 gallons.
d. Aeration rate: 10 L (STP) per minute.
e. Back pressure 5 lbs per in$^2$.
f. Dissolved oxygen: Above 20% of air saturation value.
g. Absorbance of light (wavelength 550 nm) by the fermenting medium. $A_{550}$.

2. Induction Period a. Temperature of medium.
   (1) 42° C. for the first hour of induction.
   (2) 40° C. for remainder of induction period.
b. Agitator speed: 1200 RPM.
c. Energy input by agitator: 0.5–1.5 horsepower per 100 gallons.
d. Aeration rate 10 L (STP) per minute.
e. Back pressure: 3–6 lbs per in$^2$.
f. Dissolved oxygen: preferably above 20% of air saturation. In order to obtain these values, the inlet air is enriched with oxygen.
g. Final absorbance: $A_{550}$ of 118–153.

Recovery of Δ7-pGH from E. coli Cells

The cells obtained from 200 liters of fermentation broth produced in a pilot plant by procedures described above for the 10-liter fermentor were separated from the broth by centrifugation and resuspended in 50 liters of a buffer containing EDTA (20 mM) and NaH$_2$PO$_4$ (100 mM), adjusted to pH 7.8 with sodium hydroxide. The cell suspension was passed through a Manton-Gaulin homogenizer two to three passes at a pressure of 8,000 psig in order to disrupt the cells. Intact inclusion bodies of Δ7-pGH were collected by centrifugation (13,000 g, 10 minutes) and thus separated from cellular debris. The recovered inclusion bodies (7,000 grams) were then washed in a buffer containing EDTA (10 mM), and a NaH$_2$PO$_4$ (0.2 M) adjusted to pH 7.5 with sodium hydroxide. The inclusion bodies were recovered from the washing buffer by centrifugation and dissolved in 460 liters of 8 M guanidine hydrochloride and 60 mM ethanolamine adjusted to pH 9.0 with sodium hydroxide. The solution was stirred for 12 hours to complete the unfolding of the pGH molecules.

Guanidine hydrochloride was removed from the solution by diafiltration through PM-10 membranes in the form of hollow fibers. The membranes had an average pore size of 15 Å which allows passage of molecules having molecular weights of 10,000 or less. After nearly all the guanidine hydrochloride had been removed from the solution, the solution was centrifuged at 13,000 g for 10 minutes in order to remove proteinaceous impurities and pGH molecular aggregates which precipitated out of the solution upon removal of the guanidine hydrochloride. The pGH was then purified by ion exchange chromatography using a Whatman DE-52 ion exchange gel (DEAE Cellulose) loaded into a 25 centimeter by 15 centimeter column. The solution containing the soluble, renatured pGH was loaded onto the column and the pGH was collected in the run through effluent which did not bind to the column. Column fouling and plugging, which had been observed during ion exchange chromatography when a similar urea-based recovery process was employed, was not apparent. The ion exchange chromatography step was repeated if the desired purity was not achieved.

The solution containing the pGH was then further purified by ultrafiltration through a PM-10 hollow fiber membrane to yield a solution containing 0.2% pGH. Low molecular weight contaminants were then removed by ultrafiltration against Cornell buffers. This procedure was done a first time against 50% Cornell buffer (Na$_2$CO$_3$, 11 mM; NaHCO$_3$, 13 mM) and a second time against 2% Cornell buffer (Na$_2$CO$_3$, 0.42 mM; NaHCO$_3$, 0.50 mM). The solution was then concentrated by ultrafiltration through PM-10 hollow fibers to yield a solution containing 0.2% to 2% pGH. The solution was then centrifuged and the supernatant was filtered through a 0.2 micron pore filter. The pGH in the solution was then lyophilized to produce pGH in a powdered, bioactive form.

EXAMPLE II

This example deals with the production of bovine growth hormone (bGH). The transformant cells used for this example were made by the following method.

Sample of E. coli HB101 (pL-mu-Δ9 bGH and pCI857) cells, ATCC 53030, to which 4% (v/v) glycerol had been added, were stored under liquid nitrogen until needed.

The inoculum for a 9-liter fermentor charge was obtained by adding the cells to duplicate 500 ml baffled flasks each containing 200 mL of LB medium. The LB medium had the following composition: 10 g per L tryptone, 5 g per L yeast extract, 10 g per liter NaCl, 100 ug/ml ampicillin plus 50 ug/ml kanamycin. The pH of the medium was adjusted to a value of 7.0. The flasks were closed with a milk filter closure so that some aeration of the medium could take place while the flasks were shaken at 200 rpm for 15–20 hours at 30° C. in a New Brunswick shaker.

The fermentor was a New Brunswick Microgen with a total volume of 16 liters. Nine liters of liquid medium were initially charged to the fermentor plus 400 ml of inoculum. $A_{550}$ of inoculum = 4–6.

A. Fermentation Medium

The composition of the initial 9 liters of medium is shown below:

| Product | Concentration Grams/Liter |
| --- | --- |
| NZ Amine A-Sheffield | 33.0 |
| Glycerol | 55.0 |
| (NH$_4$)$_2$SO$_4$ | 5.6 |
| K$_2$HPO$_4$ | 6.7 |
| NaH$_2$PO$_4$ | 3.3 |
| Na Citrate | 1.1 |

-continued

| Product | Concentration Grams/Liter |
|---|---|
| $MgSO_4.7H_2O$ | 7.8 |
| Hodag K-67 Antifoam | 5 ml |
| $FeCl_3.6H_2O$ | 0.014 |
| ZnO | 0.0014 |
| $CuCl_2.2H_2O$ | 0.00028 |
| $Co(NO_3)_2.6H_2O$ | 0.00028 |
| $(NH_4)_2MoO_4$ | 0.00028 |
| EDTA (disodium salt) | 0.14 |

The medium was sterilized at 15 psig steam pressure (121° C. for 15 to 20 minutes) and the pH was adjusted to 6.8 with NaOH.

To the medium, ampicillin and kanamycin were added in sufficient amount to give a concentration of 25 mg/L for each antibiotic. The solution of antibiotics was sterilized by filtration.

During the fermentation, three additional feedings of nutrients were added to the fermentor. The first feeding (at an $A_{550}=30-35$) consisted of 250 g of NZ Amine A and 250 g of glycerol dissolved in one liter of water. This allows the cell density to increase to $A_{550}$ of 50–60 before temperature induction. At cell densities of 50–60 (23–25 hours after inoculation), the fermentor was again fed 250 g NZ Amine A plus 250 g glycerol and the bacteria were induced to synthesize bGH by raising the temperature to 42° C. for one hour. At an $A_{550}=90-100$, a final feeding of 125 g NZ Amine A plus 125 g glycerol was added so that nutrients were available for the remaining induction period.

B. Fermentor Operation

The operating conditions that gave the best results are set forth in this section.

1. Time Period: 0–24 Hours a. Temperature of medium=28° C.
b. Agitator speed: 1000 RPM.
c. Energy input by agitator: 0.5–1.5 horsepower per 100 gallons.
d. Aeration rate: 10 L (STP) per minute.
e. Back pressure: 3 lbs per in$^2$.
f. Dissolved oxygen: 50% of air saturation value.
g. Additional feeding at 16 hours. $A_{550}=30-35$.
h. Absorbance of light (wavelength 550 nm) by the fermenting medium. $A_{550}$ at induction=50–60 by 24 hrs.

2. Time Period: 24–32 Hours a. Temperature of medium.
  (1) 42° C. for 24–25th hours.
  (2) 40° C. for 25–32nd hours.
b. Agitator speed: 1200 RPM.
c. Energy input by agitator: 1.0–2.0 horsepower per 100 gallons.
d. Aeration rate: 10 L (STP) per minute.
e. Back pressure: 3–6 lbs per in$^2$.
f. Dissolved oxygen: 10–40% of air saturation. In order to obtain these values, the inlet air is enriched with oxygen and mixed prior to introduction to the fermentor through the main sparger.
g. Final absorbance: $A_{550}$ of 100–123.
h. Additional feedings at 24 hours and at 29 hours.

C. Results

The results obtained from three typical runs using the procedures specified above were as follows.

| Final Assays of Fermentation Medium for Δ9-bGH. Assay Method High Performance Liquid Chromatography (HPLC) | | | |
|---|---|---|---|
| Run No. | Back Pressure Lbs. per in$^2$ | Final Absorbance $A_{550nm}$ | Number of Cells per ml (Final) | Bovine Growth Hormone Grams per Liter (HPLC) |
| 52 | 5 | 112 | $5 \times 10^{10}$ | 3.73 |
| 53 | 3 | 99 | $5 \times 10^{10}$ | 3.61 |
| 54 | 3 | 123 | $5 \times 10^{10}$ | 5.93 |

The conditions used in the foregoing fermentations in the 10-liter fermentor were used in a pilot plant to produce larger quantities of bovine growth hormone, Δ9-bGH.

Recovery of Δ9-bGH from *E. coli* Cells

The cells obtained from 86 liters of fermentation broth produced in a pilot plant by procedures described above for the 10-liter fermentor were separated from the broth by centrifugation and resuspended in 50 liters of a buffer containing EDTA (20 mM) and $NaH_2PO_4$ (100 mM), adjusted to pH 7.8 with sodium hydroxide. The cell suspension was passed through a Manton-Gaulin homogenizer two to three passes at a pressure of 8,000 psig in order to disrupt the cells. Intact inclusion bodies of Δ9-bGH were collected by centrifugation (13,000 g, 10 minutes) and thus separated from cellular debris. The recovered inclusion bodies (7,000 grams) were then washed in a buffer containing EDTA (10 mM), and a $NaH_2PO_4$ (0.2 M) adjusted to pH 7.5 with sodium hydroxide. The inclusion bodies were recovered from the washing buffer by centrifugation and dissolved in 200 liters of 8 M guanidine hydrochloride and 60 mM ethanolamine adjusted to pH 9.0 with sodium hydroxide. The solution was stirred for 12 hours to complete the unfolding of the pGH molecules.

Guanidine hydrochloride was removed from the solution by diafiltration through PM-10 membranes in the form of hollow fibers. The membranes had an average pore size of 15 Å which allows passage of molecules having molecular weights of 10,000 or less. After all the guanidine hydrochloride had been removed from the solution, the solution was centrifuged at 13,000 g for 10 minutes in order to remove proteinaceous impurities and bGH molecular aggregates which precipitated out of the solution upon removal of the guanidine hydrochloride. The pGH was then purified by ion exchange chromatography using a Whatman DE-52 ion exchange gel (DEAE Cellulose) loaded into a 25 centimeter by 15 centimeter column. The solution containing the soluble, renatured bGH was loaded onto the column and the bGH was collected in the run through effluent which did not bind to the column. Column fouling and plugging, which had been observed during ion exchange chromatography when the urea-based recovery process was employed, was not apparent. The ion exchange chromatography step was repeated if the desired purity was not achieved.

The solution containing the bGH was then further purified by ultrafiltration through a PM-10 hollow fiber membrane to yield a solution containing 0.2% bGH. Low molecular weight contaminants were then removed by ultrafiltration against Cornell buffers. This procedure was done a first time against 50% Cornell buffer and a second time against 2% Cornell buffer. The solution was then concentrated by ultrafiltration through PM-10 hollow fibers to yield a solution containing 0.2% to 2% bGH. The solution was then centrifuged and the supernatant was filtered through a 0.2 micron pore filter. The bGH in the solution was then lyophilized to produce bGH in a powdered, bioactive form.

What is claimed is:

1. A process for recovering and purifying monomeric, biologically active growth hormone from insoluble inclusion bodies produced by expression of a heterologous gene in a microorganism, which process comprises:
    (a) solubilizing and denaturing the growth hormone by extracting the inclusion bodies into a solution of a guanidine salt;
    (b) renaturing at least a portion of the growth hormone in the solution and inducing precipitation of at least a portion of contaminant proteins and aggregates in the solution by replacing the guanidine salt solution with a denaturant-free buffer solution without the use of an intermediate denaturant, thereby reducing the presence of soluble contaminant proteins and agregates in the renatured protein solution which tend to foul the chromatography column and which are not biologically active;
    (c) removing the precipitated contaminants and aggregates from the denaturant-free buffer solution; and
    (d) purifying the monomeric growth hormone in the solution by ion exchange chromatography.

2. A process as claimed in claim 1, wherein the guanidine salt is guanidine hydrochloride.

3. A process as claimed in claim 2, wherein the guanidine hydrochloride solution has a concentration from about 6 to about 8 M.

4. A process as claimed in claim 3, wherein the guanidine hydrochloride solution also contains ethanolamine at a concentration from about 20 mM to 100 mM.

5. A process as claimed in claim 4, wherein the inclusion bodies are dissolved in the guanidine hydrochloride solution in an amount sufficient to give a growth hormone concentration of from about 1 to about 2.5 grams per liter.

6. A process as claimed in claim 2, wherein the solution of growth hormone in guanidine hydrochloride is allowed to stand for a period of from about 6 to about 36 hours prior to renaturation.

7. A process as claimed in claim 2, wherein the guanidine salt is removed by diafiltration or dialysis.

8. A process as claimed in claim 2, wherein the guanidine salt is removed over a period of less than about 10 hours.

9. A process as claimed in claim 2, wherein the growth hormone is porcine growth hormone or a biologically active fragment or analog thereof.

10. A process as claimed in claim 2, wherein the growth hormone is bovine growth hormone or a biologically active fragment or analog thereof.

11. A process as claimed in claim 2, wherein, prior to solubilizing the inclusion bodies, the inclusion bodies are washed in a buffered solution which is devoid of detergents, reducing agents and enzymes.

12. A process as claimed in claim 11, wherein the solution in which the inclusion bodies are washed contains ethylenediaminetetraacetic acid and monosodium phosphate.

13. A process for recovering and purifying monomeric, biologically active porcine growth hormone, bovine growth hormone, or biologically active fragments or analogs thereof from insoluble inclusion bodies produced by expression of a heterologous gene in a microorganism, which process consists essentially of:
    (a) washing the inclusion bodies in a buffered solution which is devoid of detergents, reducing agents and enzymes;
    (b) solubilizing and denaturing the growth hormone by extracting the inclusion bodies into about a 6 to 8 M solution of a guanidine hydrochloride;
    (c) renaturing at least a portion of the growth hormone in the solution and inducing precipitation of at least a portion of contaminant proteins and aggregates in the solution by replacing the guanidine hydrochloride solution with a denaturant-free buffer solution without the use of an intermediate denaturant, thereby reducing the presence of soluble contaminant proteins and aggregates in the renatured protein solution which tend to foul the chromatography column and which are not biologically active;
    (d) removing the precipitated contaminants and aggregates from the denaturant-free buffer solution; and
    (e) purifying the monomeric growth hormone in the solution by ion exchange chromatography.

14. A process as claimed in claim 13, wherein the guanidine hydrochloride solution also contains ethanolamine at a concentration from about 20 mM to 100 mM.

15. A process as claimed in claim 14, wherein the inclusion bodies are dissolved in the guanidine hydrochloride solution in an amount sufficient to give a growth hormone concentration of from about 1 to about 2.5 grams per liter.

16. A process as claimed in claim 13, wherein the solution of growth hormone in guanidine hydrochloride is allowed to stand for a period of from about 6 to about 36 hours prior to renaturation.

17. A process as claimed in claim 13, wherein the guanidine hydrochloride is removed by diafiltration or dialysis.

18. A process as claimed in claim 13, wherein the guanidine hydrochloride is removed over a period of less than about 10 hours.

19. A process as claimed in claim 13 wherein the solution in which the inclusion bodies are washed contains ethylenediaminetetraacetic acid and monosodium phosphate.

* * * * *

UNITED STATES PATENT AND TRADEMARK OFFICE
CERTIFICATE OF CORRECTION

PATENT NO. : 4,705,848
DATED : November 10, 1987
INVENTOR(S) : Ren-Der Yang et al It is certified that error appears in the above-identified patent and that said Letters Patent are hereby corrected as shown below:

Column 10, line 12, following the table, insert -- Level of expression $7 \times 10^6$ molecules of 9-bGH per cell --

Signed and Sealed this

Seventh Day of June, 1988

Attest:

Attesting Officer

DONALD J. QUIGG

Commissioner of Patents and Trademarks